US012575869B2

(12) United States Patent
Chappuis et al.

(10) Patent No.: US 12,575,869 B2
(45) Date of Patent: Mar. 17, 2026

(54) COMPLIANT ORTHOPEDIC DRIVER

(71) Applicant: GLOBUS MEDICAL, INC., Audubon, PA (US)

(72) Inventors: Olivier Chappuis, Lutry (CH); Szymon Kostrzewski, Lausanne (CH)

(73) Assignee: Globus Medical Inc., Audubon, PA (US)

( * ) Notice: Subject to any disclaimer, the term of this patent is extended or adjusted under 35 U.S.C. 154(b) by 0 days.

(21) Appl. No.: 18/909,070

(22) Filed: Oct. 8, 2024

(65) Prior Publication Data

US 2025/0090211 A1 Mar. 20, 2025

Related U.S. Application Data

(63) Continuation of application No. 18/528,855, filed on Dec. 5, 2023, now Pat. No. 12,121,278, which is a continuation of application No. 17/726,696, filed on Apr. 22, 2022, now Pat. No. 11,832,863, which is a continuation of application No. 16/180,381, filed on Nov. 5, 2018, now Pat. No. 11,337,742.

(51) Int. Cl.
| | |
|---|---|
| *A61B 17/88* | (2006.01) |
| *A61B 34/30* | (2016.01) |
| *A61B 17/00* | (2006.01) |
| *A61B 17/90* | (2006.01) |
| *A61B 34/20* | (2016.01) |

(52) U.S. Cl.
CPC .......... *A61B 17/8875* (2013.01); *A61B 34/30* (2016.02); *A61B 2017/00862* (2013.01); *A61B 17/90* (2021.08); *A61B 2034/2072* (2016.02)

(58) Field of Classification Search
CPC ............ A61B 17/8875; A61B 17/8877; A61B 17/888; A61B 17/8883; A61B 17/8886; A61B 17/8888; A61B 17/8891
See application file for complete search history.

(56) References Cited

U.S. PATENT DOCUMENTS

| | | |
|---|---|---|
| 4,150,293 A | 4/1979 | Franke |
| 5,246,010 A | 9/1993 | Gazzara et al. |
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |

(Continued)

OTHER PUBLICATIONS

US 8,231,638 B2, 07/2012, Swarup et al. (withdrawn)

*Primary Examiner* — Si Ming Ku

(57) ABSTRACT

Embodiments of a compliant orthopedic driver are disclosed herein. In some embodiments, compliant orthopedic driver includes a body extending from a proximal end to a distal end along a driver axis; a driver tip disposed at the distal end of the body, wherein the body includes at least one compliant portion configured to allow the driver flex about at least two axes transverse to the driver axis.

19 Claims, 6 Drawing Sheets

(56)         References Cited

U.S. PATENT DOCUMENTS

| | | | |
|---|---|---|---|
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |

(56) References Cited

U.S. PATENT DOCUMENTS

| | | |
|---|---|---|
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Willliams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,263,933 B2 | 9/2012 | Zeile |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |

(56)　　　　　References Cited

U.S. PATENT DOCUMENTS

| | | | |
|---|---|---|---|
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 12/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |

(56) References Cited

U.S. PATENT DOCUMENTS

| | | |
|---|---|---|
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0130810 A1 | 5/2014 | Azizian et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |

(56) References Cited

U.S. PATENT DOCUMENTS

| | | |
|---|---|---|
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1* | 10/2014 | Farritor ................ A61B 46/10 |
| | | 600/102 |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |

* cited by examiner

COMPLIANT ORTHOPEDIC DRIVER

CROSS REFERENCE TO RELATED APPLICATIONS

This patent application is a continuation of U.S. patent application Ser. No. 18/528,855 filed on Dec. 5, 2023, which is a continuation of patent application Ser. No. 17/726,696 filed on Apr. 22, 2022, which is a continuation of patent application Ser. No. 16/180,381 filed on Nov. 5, 2018, all of which are incorporated in their entirety herein.

FIELD OF THE INVENTION

The invention generally relates to devices and methods that improve surgical procedures by, for example, providing a working space for the procedure and improving the surgical conditions for the practitioner of a procedure.

BACKGROUND OF THE INVENTION

During spinal, orthopedic and general surgeries, screws are often used to fix implants and other mechanical constructs to bony structure. There are an increasing number of robotic systems and various types of instrument guides available on the market. The goal of such apparatuses is to assist surgeons in drilling, tapping and/or screw placement along a desired trajectory. The usage of guides and robotic systems to maintain the desired trajectory can lead to undesirable locking between the driver (e.g., a screwdriver) and the fixation element (e.g., a screw) in a manner which makes it difficult to decouple the driver from the fixation element. This difficult can negatively impact the surgical procedure and possibly the final result of the procedure.

For example, in the case of pedicle screw placement along a spine, a guide (robotic or handheld) is first used to guide a drill in the direction of a desired trajectory. Subsequently, the drill is inserted through the guide to begin drilling the hole in a vertebra. However, upon contact with the bone, contact forces (action and reaction) may cause the less rigid structure (typically the bone/vertebra) to move away from its initial position. If the trajectory of the drill is not corrected to compensate for these contact forces, the actual drilled trajectory will not be aligned with the desired trajectory. After the hole is drilled, other hole preparation tasks may be performed (e.g., tapping, bone breach testing, etc.). Finally, the implant is placed in the bone. Since implants do not typically have cutting abilities, the implant (e.g., a screw) follows the drilled hole trajectory. Because the driver being used to install the implant extends through the guide, which extends along the desired trajectory, and the implant extends along the drilled hole trajectory, which is not collinear with the desired trajectory, there will be action-reaction forces and torques at the interface of the implant and the driver. This interface is typically configured to have minimal mechanical backlash and a rigid connection (e.g., torx interface, hex interface, etc.). However, this interface does not adapt well to off-axis use and, as such, will result in the locking of the driver in the implant. The principal, underlying cause of this locking is over-constraint in the driver. When the driver is locked in the implant and cannot be decoupled therefrom, typical troubleshooting techniques are moving the guide, which may delay the surgery and/or result in improper implantation of the implant.

Therefore, a need exists for an orthopedic driver that overcomes or minimizes these and other problems.

SUMMARY

Embodiments of a compliant orthopedic driver are disclosed herein. In some embodiments, compliant orthopedic driver includes a body extending from a proximal end to a distal end along a driver axis; a driver tip disposed at the distal end of the body, wherein the body includes at least one compliant portion configured to allow the driver flex about at least two axes transverse to the driver axis.

Embodiments of a compliant orthopedic driver are disclosed herein. In some embodiments, compliant orthopedic driver includes a body extending from a proximal end to a distal end along a driver axis; a driver tip disposed at the distal end of the body, wherein the body includes at least one compliant portion configured to allow the driver flex about at least two axes transverse to the driver axis wherein the body includes a first compliant portion and a second compliant portion spaced apart from the first compliant portion, and wherein each of the first and second compliant portions are configured to allow the driver flex about at least two axes transverse to the driver axis.

BRIEF DESCRIPTION OF THE DRAWINGS

The invention will be more readily understood with reference to the embodiments thereof illustrated in the attached figures, in which.

DETAILED DESCRIPTION

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Typically, an orthopedic driver (e.g., a screwdriver) requires the two degrees of freedom (DOFs) to be locked in order to fulfil its main function (i.e., insert a screw): (1)

Rotation around the driver axis and (2) translation along the driver axis. This means that when an implant is attached to the driver tip, the implant should not be able to rotate around nor translate along the driver axis. When the four remaining DOFs between driver and implant are also locked, a mechanical over-constrain results at the implant-driver interface due to non-collinearity of a trajectory of a hole drilled into a bone and instrument guiding trajectory. This over-constrain is the root cause of screw locking issues.

As such, it is necessary to add compliance to the driver to allow the driver tip to adapt or flex to the screw trajectory and, therefore, eliminate the mechanical over-constrain at the implant-driver interface. One way to add compliance to the driver is to incorporate a kinematic chain into the driver. In some embodiments, the kinematic chain may include two or more universal joints in series, each of which adds two DOFs (rotation about a first axis and rotation about a second axis) for a total of four DOFs. In other embodiments, the kinematic chain may include a universal joint (two DOFs, as explained above) and a semi-ball joint (three DOFs-rotation about three axes).

Figures 1A, 1B, 1C:
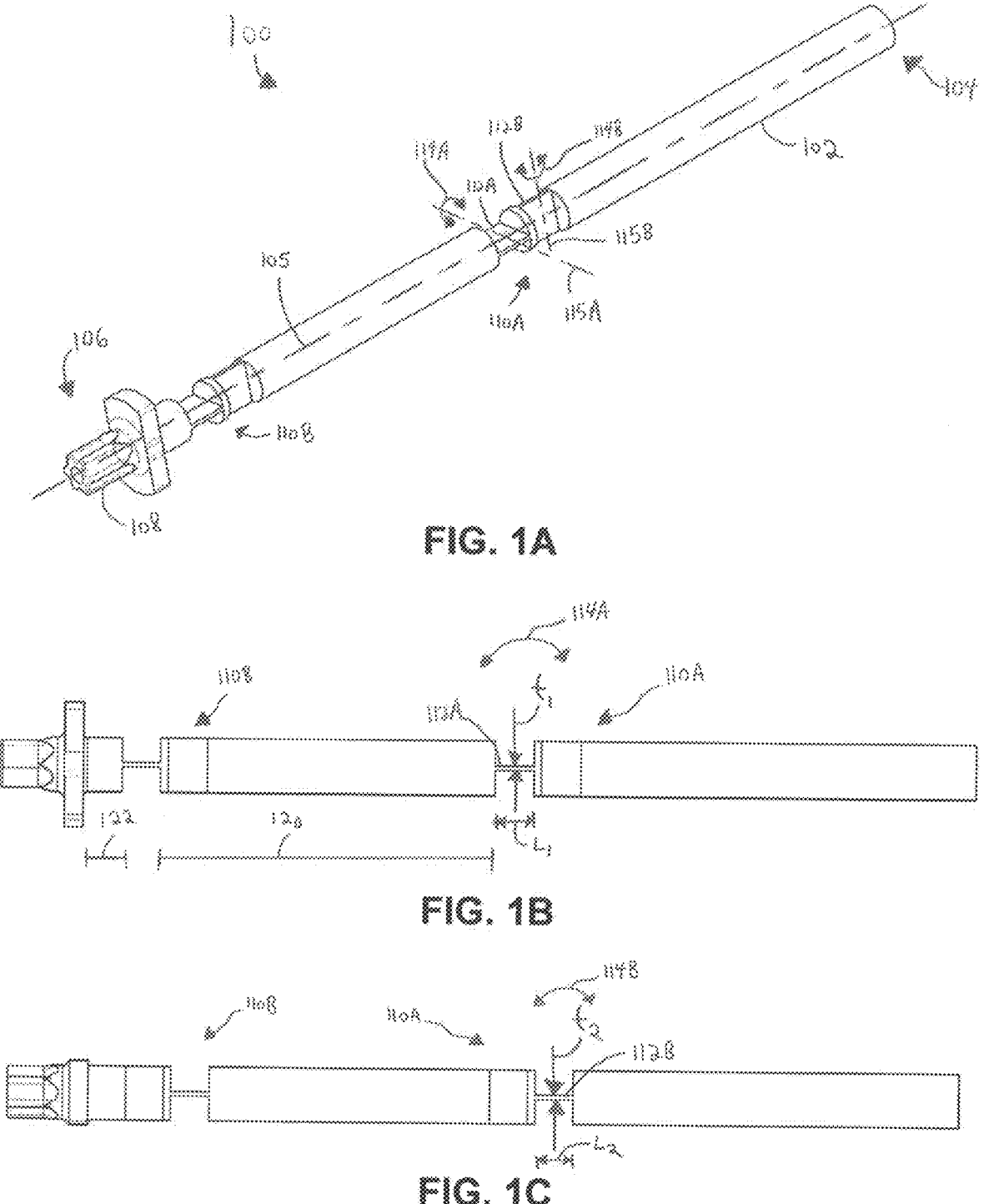
FIG. 1A is an isometric view of a compliant driver in accordance with an embodiment of the present disclosure.
FIG. 1B is a front view of the compliant drive of FIG. 1A.
FIG. 1C is a top view of the compliant driver of FIG. 1A.

FIGS. 1A-1C depict a compliant orthopedic driver 100 (e.g., a screwdriver) in accordance with embodiments of the present disclosure. In some embodiments, the driver 100 includes a body 102 extending from a proximal end 104 to a distal end 106 along a driver axis 105. The body 102 terminates at a driver tip 108 at the distal end 106. The driver tip 108 may have any shape (e.g., torx, hex, cross, etc.) corresponding to the shape of a recess in the head of a screw (not shown) to be implanted using the driver 100. In the embodiment depicted in FIGS. 1A-1C, the two universal joints are implemented by two pairs of blade hinges 110A, 110B. The two pairs of blade hinges 110A, 110B are separated by a first distance 120. The second pair of blade hinges 110B is disposed a second distance 122 from the driver tip 108. The first and second distances 120, 122 depend on the surgical procedure (e.g., spine, trauma, etc.) and the tools being used (e.g., robotic guide, handheld guide, etc.). In this embodiment, the driver tip 108 exhibits 4 DOFs. The two locked DOFs are the rotation around and translation along the driver axis 105. In some embodiments, mechanical end-stops (not shown) may be incorporated to protect the hinges against over travel.

Because each pair of hinges is identical, the first pair of blade hinges 110A will be described for brevity. The first pair of blade hinges 110A includes a first blade 112A and a second blade 112B which extends transversely to the first blade 112A. In some embodiments, the second blade 112B is perpendicular to the first blade 112A. The first blade 112A has a first length $L_1$ and a first thickness $t_1$ and the second blade has a second length $L_2$ and a second thickness $t_2$. In some embodiments, the first length $L_1$ is equivalent to the second length $L_2$. In some embodiment, the first thickness $t_1$ is equivalent to the second thickness $t_2$. The first length $L_1$ and the first thickness $t_1$ are configured to allow the driver 100 to flex about a first axis 115A as indicated by arrow 114A. Similarly, the second length $L_2$ and the second thickness $t_2$ are configured to allow the driver 100 to flex about a second axis 115B as indicated by arrow 114B. In some embodiments, the first and second axes 115A, 115B are perpendicular to the driver axis 105. In some embodiments, first and second blades 112A, 112B are configured to allow for a degree of flexure between 0° and 10°. In some embodiments, the first and second blades 112A, 112B are adjacent to one another, as depicted in FIGS. 1A-1C. In some embodiments, the first and second blades 112A, 112B may alternatively be spaced apart by a predetermined distance. In some embodiments, all sharp edges/corners of the blades may be rounded to reduce high stress concentrations.

Figure 1D:
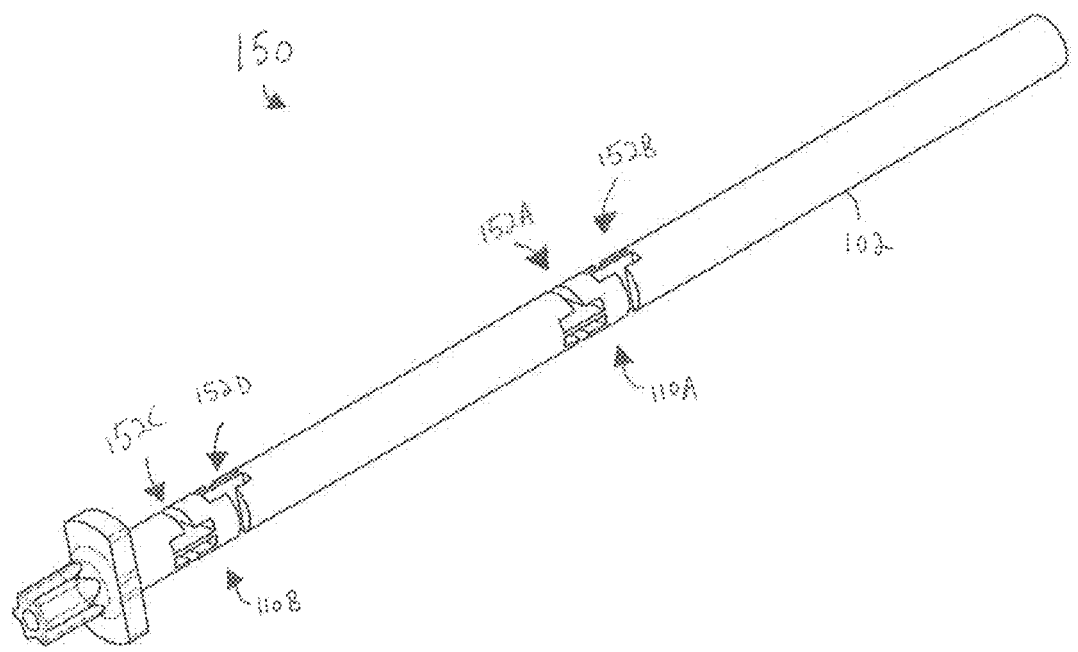
FIG. 1D is an isometric view of a compliant driver in accordance with an embodiment of the present disclosure.
Figure 1E:
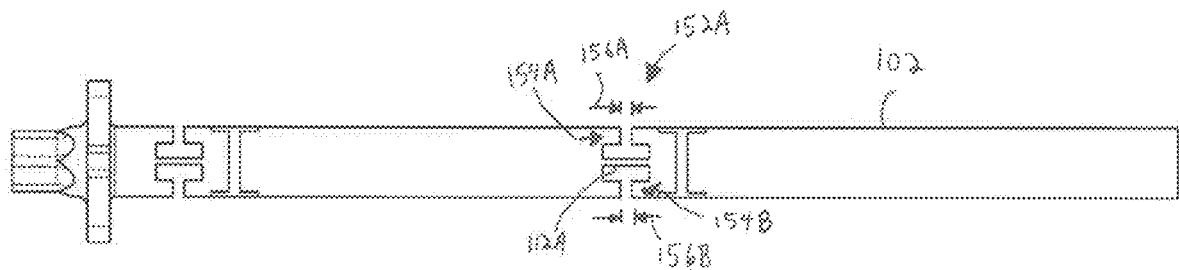
FIG. 1E is a front view of the compliant drive of FIG. 1D.

FIGS. 1D and 1E depict a compliant orthopedic driver 150 in accordance with another embodiment of the present disclosure. The driver includes all of the elements discussed above with respect to the driver 100. As such, a description of those features will be omitted here for clarity. The orthopedic driver 150 additionally includes first and second pairs of stops 152A, 152B corresponding to the first pair of blade hinges 110A and third and fourth pairs of stops 152C, 152D corresponding to the second pair of blade hinges 110B. As depicted in FIGS. 1D and 1E, each pair of stops is disposed on opposite sides of the blades to prevent over travel (i.e., limit the amount of travel) of the driver 150 in either direction of flexure. Because all four pairs of stops are substantially similar, only the first pair of stops 152A will be described. It should be understood that this description also applies to the other pairs of stops. As shown more clearly in FIG. 1E, the first pair of stops 152A includes a first pair of cantilevered portions 154A disposed on a first side of the first blade 112A and a second pair of cantilevered portions 154B disposed on a second side opposite the first side of the first blade 112A. The first and second pairs of cantilevered portions 154A, 154B extend from the body 102 over the first blade 112A. The first pair of cantilevered portions 154A are separated by a first predetermined distance 156A. The second pair of cantilevered portions 154B are separated by a second predetermined distance 156B. In some embodiments, the first and second predetermined distances 156A, 156B are equivalent; such that the amount flexure in both directions is equally limited. In some embodiments, the first and second predetermined distances 156A, 156B are not equivalent; such that flexure in one direction is limited more than flexure in the opposite direction.

Figure 2A:
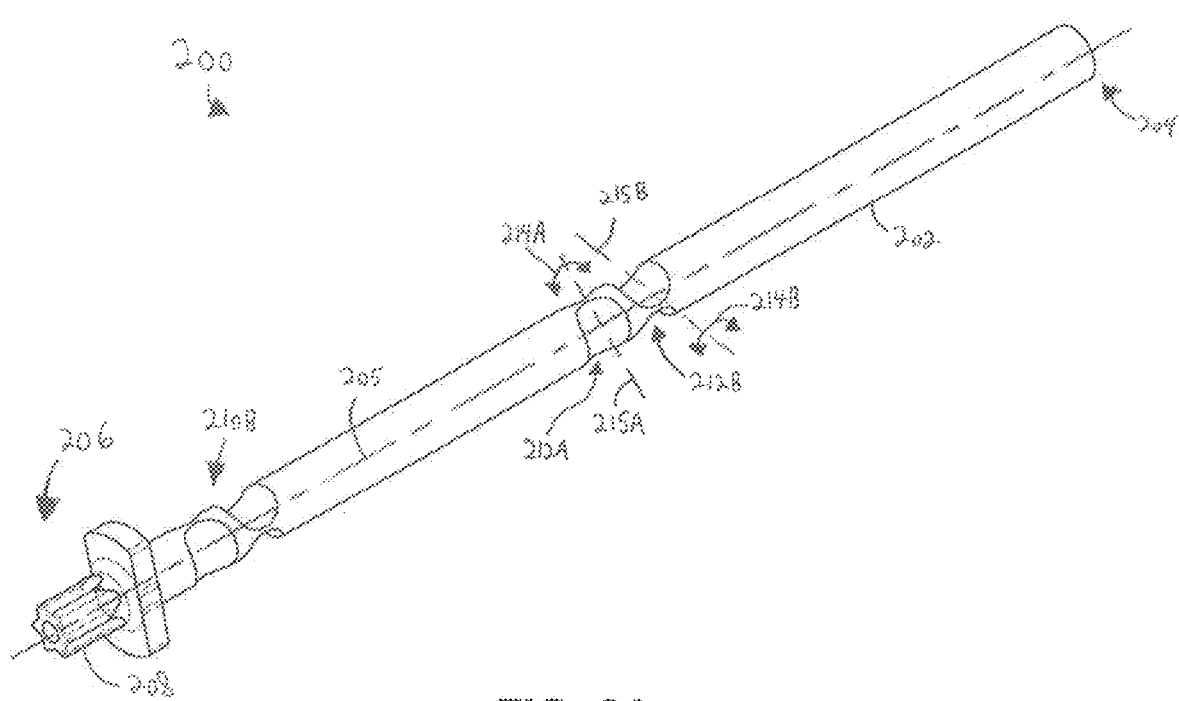
FIG. 2A is an isometric view of a compliant driver in accordance with another embodiment of the present disclosure.
Figure 2B:
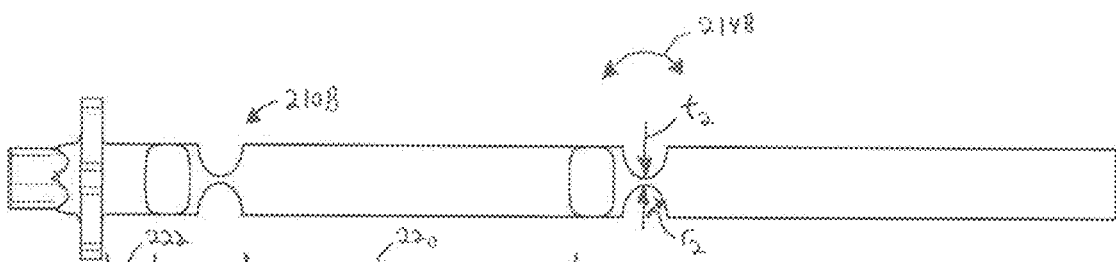
FIG. 2B is a front view of the compliant drive of FIG. 2A.
Figure 2C:
FIG. 2C is a top view of the compliant driver of FIG. 2A.

FIGS. 2A-2C depict a compliant orthopedic driver 200 (e.g., a screwdriver) in accordance with another embodiment of the present disclosure. The driver 200 functions similarly to the drive 100 described above. In some embodiments, the driver 200 includes a body 202 extending from a proximal end 204 to a distal end 206 along a driver axis 205. The body 202 terminates at a driver tip 208 at the distal end 206. The driver tip 208 may have any shape (e.g., torx, hex, cross, etc.) corresponding to the shape of a recess in the head of a screw (not shown) to be implanted using the driver 200. In the embodiment depicted in FIGS. 2A-2C, the two universal joints are implemented by two pairs of notch hinges 210A, 210B. The two pairs of notch hinges 210A, 210B are separated by a first distance 220. The second pair of notch hinges 210B is disposed a second distance 222 from the driver tip 208. The first and second distances 220, 222 depend on the surgical procedure (e.g., spine, trauma, etc.) and the tools being used (e.g., robotic guide, handheld guide, etc.). In this embodiment, the driver tip 208 also exhibits 4 DOFs. The two locked DOFs are again the rotation around and translation along the driver axis 205. In some embodiments, mechanical end-stops (not shown) may be incorporated to protect the hinges against over travel.

Because each pair of hinges is identical, the first pair of notch hinges 210A will be described for brevity. The first pair of notch hinges 210A includes a first pair of notches 212A and a second pair of notches 212B which extends transversely to the first blade 212A. In some embodiments, the second pair of notches 212B are angularly offset with respect to the first pair of notches 212A by 90°. Each of the first pair of notches 212A has a first radius $r_1$. A first thickness $t_1$ separates the first pair of notches 212A (FIG. 2C). Each of the second pair of notches 210B has a second radius $r_2$. A second thickness $t_2$ separates the second pair of notches 212B (FIG. 2C). In some embodiments, the first radius $r_1$ is equivalent to the second radius $r_2$. In some embodiments, the first thickness $t_1$ is equivalent to the second thickness $t_2$. The first radius $r_1$ and the first thickness $t_1$ are configured to allow the driver 200 to flex about a first axis 215A as indicated by arrow 214A. Similarly, the second radius $r_2$ and the second thickness $t_2$ are configured to allow the driver 200 to flex about a second axis 215B as indicated by arrow 214B. In some embodiments, the first and second axes 215A, 215B are perpendicular to the driver axis 205. In some embodiments, first and second pairs of notches 212A, 212B are configured to allow for a degree of flexure between 0° and 10°. In some embodiments, the first and second pairs of notches 212A, 212B are adjacent to one another, as depicted in FIGS. 2A-2C. In some embodiments, the first and second pairs of notches 212A, 212B may alternatively be spaced apart by a predetermined distance. The notches 212A, 212B advantageously allow for gradual flexure without high stress areas associated with sharp corners. In some embodiments, the driver 200 may also include stops as described above with respect to FIGS. 1D and 1E to limit the amount of flexure of the driver.

Figure 3A:
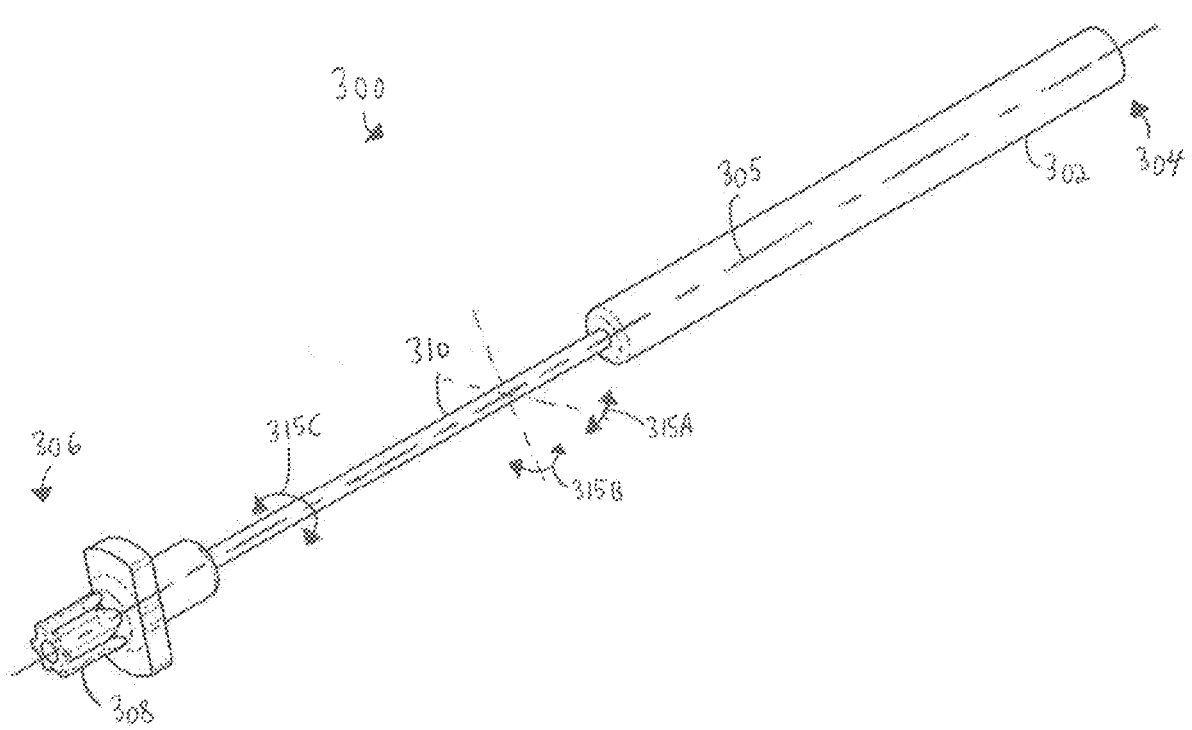
FIG. 3A is an isometric view of a compliant driver in accordance with another embodiment of the present disclosure.
Figure 3B:
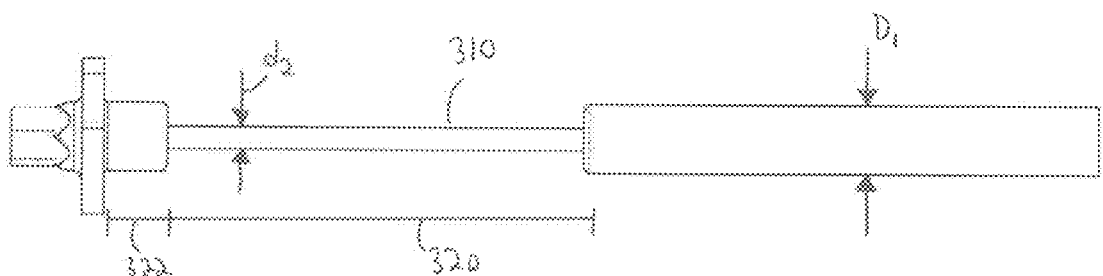
FIG. 3B is a front view of the compliant driver of FIG. 3A.

FIGS. 3A and 3B depict a compliant orthopedic driver 300 (e.g., a screwdriver) in accordance with another embodiment of the present disclosure. The driver 300 functions somewhat similarly to the drivers 100, 200 described above. In some embodiments, the driver 300 includes a body 302 extending from a proximal end 304 to a distal end 306 along a driver axis 305. The body 302 terminates at a driver tip 308 at the distal end 306. The driver tip 308 may have any shape (e.g., torx, hex, cross, etc.) corresponding to the shape of a recess in the head of a screw (not shown) to be implanted using the driver 300. The driver 300 incorporates the semi-ball joint method, which is implemented by having a reduced diameter section 310. The reduced diameter section provides 5 DOFs: flexure about a first axis 314A, slight translation along the first axis 314A, flexure about a second axis 314B, slight translation along the second axis 314B, and torsion about the driver axis 305.

The reduced diameter section 310 has a first length 320 and is disposed a first distance 322 from the driver tip 308. The first length 320 and the first distance 322 depend on the surgical procedure (e.g., spine, trauma, etc.) and the tools being used (e.g., robotic guide, handheld guide, etc.). The reduced diameter section 310 has a second diameter $d_2$, which is smaller than a first diameter $d_1$ of the body 302. The first length 320 and the second diameter d2 dictate the amount of flexure of the driver 300. In some embodiments, the first length 320 and the diameter of the reduced diameter section 310 may be configured to allow for slight torsion about the driver axis 305. As such, the only fully locked DOF is the translation along the driver axis 305. The first length 320 is configured to allow for more torsion stiffness than flexure stiffness. In some embodiments, the driver 300 may also include stops as described above with respect to FIGS. 1D and 1E to limit the amount of flexure of the driver.

Figure 4A:
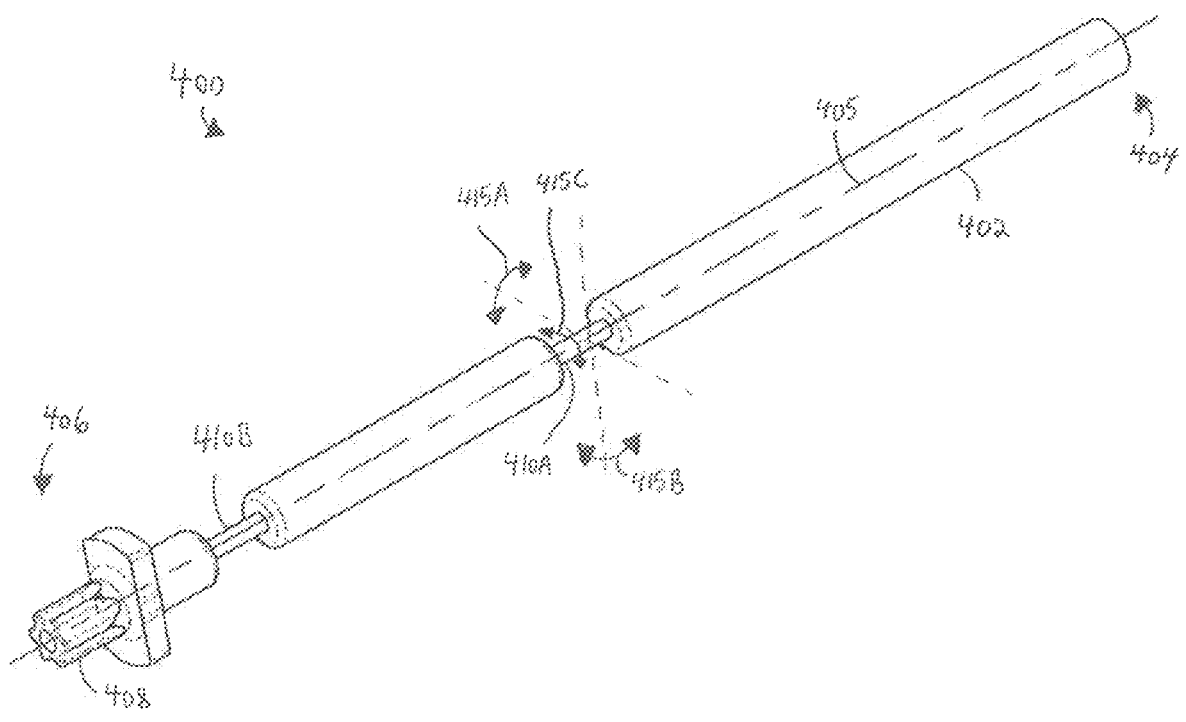
FIG. 4A is an isometric view of a compliant driver in accordance with another embodiment of the present disclosure.
Figure 4B:
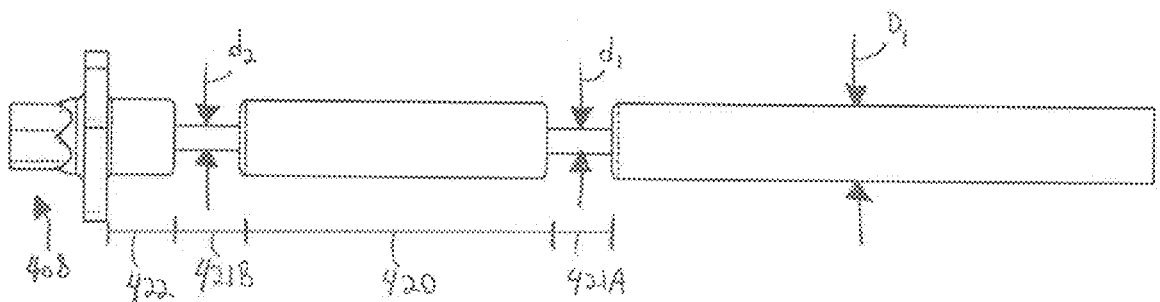
FIG. 4B is a front view of the compliant driver of FIG. 4A.

FIGS. 4A and 4B depict a compliant orthopedic driver 400 (e.g., a screwdriver) in accordance with another embodiment of the present disclosure. The driver 400 functions similarly to the driver 300 described above. In some embodiments, the driver 400 includes a body 402 extending from a proximal end 404 to a distal end 406 along a driver axis 405. The body 402 terminates at a driver tip 408 at the distal end 406. The driver tip 408 may have any shape (e.g., torx, hex, cross, etc.) corresponding to the shape of a recess in the head of a screw (not shown) to be implanted using the driver 400.

The driver 400 also incorporates the semi-ball joint method, which is implemented by having a first reduced diameter section 410A and a second reduced diameter section 410B.

Because the second reduced diameter section 410B is identical to the first reduced diameter section, only the first reduced diameter section 410A will be described for brevity. The first reduced diameter section 410A has a first length 421A and a first reduced diameter $d_1$, which is less than a body diameter $D_1$. The first reduced diameter section 410A is disposed a first distance 420 from the second reduced diameter section 410B. The second reduced diameter section 410B is disposed a second distance 422 from the driver tip 408. The first and second lengths 421A, 421B, the first and second reduced diameters $d_1$, $d_2$, and the first and second distances 420, 422 all dictate the amount of flexure of the driver 400 depend on the surgical procedure (e.g., spine, trauma, etc.) and the tools being used (e.g., robotic guide, handheld guide, etc.). In some embodiments, these dimensions may be configured to allow for slight torsion about the driver axis 305. As such, the only fully locked DOF is the translation along the driver axis 405. Each of the first and second reduced diameter sections 410A, 410B provide the same DOFs as discussed above with respect to the reduced diameter section 310. However, having two shorter reduced diameter sections advantageously provides improved resistance to buckling under an axial load. In some embodiments, the driver 400 may also include stops as described above with respect to FIGS. 1D and 1E to limit the amount of flexure of the driver.

Figures 5A, 5B:
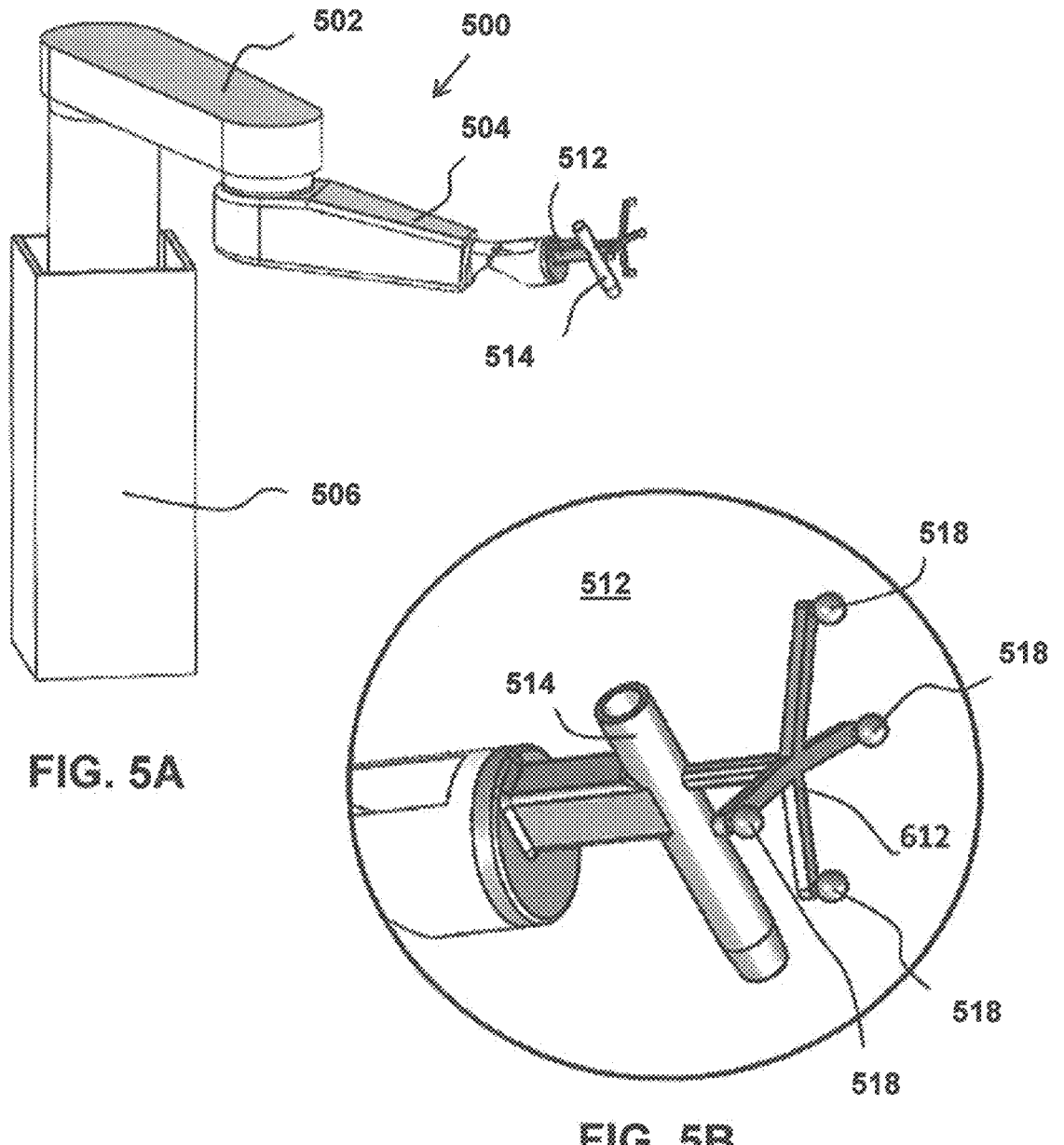
FIGS. 5A and 5B depict an exemplary robotic arm with which a compliant driver according to embodiments of the present disclosure may be used.

FIGS. 5A and 5B depict an exemplary robot arm with which a compliant driver (100, 200, 300, 400) in accordance with the present disclosure may be used. As noted above, the compliant driver (100, 200, 300, 400) may also be used with any other type of guide (e.g., handheld). FIG. 5A depicts part of a surgical robot system 500 with a robot 502 including base 506, robot arm 504, and end-effector 512. Other elements of the robot system, not illustrated, such as the display, cameras, etc. may also be present. FIG. 5B depicts a close-up view of the end-effector 512 with guide tube 514 and a plurality of tracking markers 518 rigidly affixed to the end-effector 512. In this embodiment, the plurality of tracking markers 118 are attached to the guide tube 112. When tracking an instrument such as, for example, the compliant driver (100, 200, 300, 400), the end-effector 512, or other object to be tracked in 3D, an array of tracking markers 518 may be rigidly attached to a portion of the instrument or end-effector 512. Preferably, the tracking markers 518 are attached such that the markers 518 are out of the way (e.g., not impeding the surgical operation, visibility, etc.). The markers 518 may be affixed to the instrument, end-effector 112, or other object to be tracked, for example, with an array 612.

Embodiments of the inventive driver advantageously solve the problem of driver-implant locking by preventing or substantially limiting such an occurrence by introducing adapted compliance in the driver. As a result, one exemplary realized benefit is the usability of such drivers in conjunction with robotic systems by decreasing the probability of occurrence of the implant locking effect to almost zero, without interfering with the general workflow or external functionality (proper implant function).

While the invention herein disclosed has been described with reference to specific embodiments and applications thereof, numerous modifications and variations can be made thereto by those skilled in the art without departing from the scope of the invention as set forth in the claims.

What is claimed is:

1. A method of driving a bone screw into bone comprising:

providing a compliant orthopedic driver including:

a body extending from a proximal end to a distal end along a driver axis;

a driver tip disposed at the distal end of the body;

wherein the body includes at least one compliant portion including:

a first round notch adapted to flex about a first axis transverse to the driver axis; and a second round notch longitudinally disposed from the first round notch and adapted to flex about a second axis transverse to the driver axis, the first axis being angularly offset from the second axis; and driving the bone screw into the bone using the compliant orthopedic driver.

2. The driver of claim 1, wherein the first axis is angularly offset from the second axis by 90 degrees.

3. The method of claim 1, wherein the at least one compliant portion includes a pair of oppositely disposed concave notches relative to the driver axis.

4. The method of claim 1, wherein the at least one compliant portion includes a pair of stops configured to limit an amount of flexure of the body about the at least two axes.

5. The method of claim 1, wherein the at least one compliant portion includes two compliant portions longitudinally spaced apart by a predetermined distance.

6. The method of claim 5, wherein the two compliant portions comprise a first pair of round notch hinges and a second pair of round notch hinges, each of which includes a first pair of round notches and a second pair of round notches angularly offset from the first pair of round notches.

7. The method of claim 6, wherein the first pair of round notches is perpendicular to the second pair of round notches.

8. The method of claim 6, wherein each notch of the first pair of round notches has a first predetermined radius and each notch of the second pair of round notches has a second predetermined radius, and wherein the first pair of round notches are separated by a first predetermined thickness and the second pair of round notches are separated by a second predetermined thickness.

9. The method of claim 5, wherein the two compliant portions include a first reduced diameter section having a first predetermined length and a second reduced diameter section having a second predetermined length.

10. The method of claim 1, wherein the at least one compliant portion includes a reduced diameter section having a predetermined length.

11. The method of claim 1, wherein the at least one compliant portion includes a pair of stops configured to limit an amount of flexure of the driver about the at least two axes.

12. A method of driving a bone screw into bone comprising:

providing a compliant orthopedic driver including:

a body extending from a proximal end to a distal end along a driver axis;

a driver tip disposed at the distal end of the body, wherein the body includes a first compliant portion and a second compliant portion longitudinally spaced apart from the first compliant portion along the body, and wherein each compliant portion includes:

a first round notch adapted to flex about a first axis transverse to the driver axis; and a second round notch longitudinally disposed from the first round notch and adapted to flex about a second axis transverse to the driver axis, the first axis being angularly offset from the second axis; and driving the bone screw into the bone using the compliant orthopedic driver.

13. The method of claim 12, wherein the first axis is angularly offset from the second axis by 90 degrees.

14. The method of claim 12, wherein each of the first and second compliant portions includes a pair of oppositely disposed concave notches relative to the driver axis.

15. The method of claim 12, wherein at least one of the compliant portions includes a pair of stops configured to limit an amount of flexure of the body about the at least two axes.

16. The method of claim 12, wherein the first and second compliant portions comprise a first pair of round notch hinges and a second pair of round notch hinges, each of which includes a first pair of round notches and a second pair of round notches angularly offset from the first pair of round notches.

17. The method of claim 16, wherein the first pair of round notches is perpendicular to the second pair of round notches.

18. The method of claim 16, wherein each notch of the first pair of round notches has a first predetermined radius and each notch of the second pair of round notches has a second predetermined radius, and wherein the first pair of round notches are separated by a first predetermined thickness and the second pair of round notches are separated by a second predetermined thickness.

19. The method of claim 16, wherein the first and second compliant portions include a first reduced diameter section having a first predetermined length and a second reduced diameter section having a second predetermined length.

* * * * *